US012735378B2

(12) United States Patent
Dambrin

(10) Patent No.: US 12,735,378 B2
(45) Date of Patent: Sep. 15, 2026

(54) PROCESS FOR PRODUCING PARA-EUGENOL AND/OR ORTHO-EUGENOL

(71) Applicant: SPECIALTY OPERATIONS FRANCE, Lyons (FR)

(72) Inventor: Valéry Dambrin, Irigny (FR)

(73) Assignee: SPECIALTY OPERATIONS FRANCE, Lyons (FR)

( * ) Notice: Subject to any disclaimer, the term of this patent is extended or adjusted under 35 U.S.C. 154(b) by 855 days.

(21) Appl. No.: 17/907,234

(22) PCT Filed: Mar. 22, 2021

(86) PCT No.: PCT/EP2021/057198
§ 371 (c)(1),
(2) Date: Sep. 23, 2022

(87) PCT Pub. No.: WO2021/191113
PCT Pub. Date: Sep. 30, 2021

(65) Prior Publication Data

US 2023/0118184 A1 Apr. 20, 2023

(30) Foreign Application Priority Data

Mar. 23, 2020 (FR) ........................................ 2002806

(51) Int. Cl.
*C07C 43/23* (2006.01)
*B01J 23/42* (2006.01)
*B01J 23/44* (2006.01)
*C07C 41/26* (2006.01)

(52) U.S. Cl.
CPC ............... *C07C 43/23* (2013.01); *B01J 23/42* (2013.01); *B01J 23/44* (2013.01); *C07C 41/26* (2013.01)

(58) Field of Classification Search
CPC ................................ C07C 41/26; C07C 43/23
USPC .......................................................... 568/650
See application file for complete search history.

(56) References Cited

U.S. PATENT DOCUMENTS 3,929,904 A 12/1975 De Simone et al.

FOREIGN PATENT DOCUMENTS

CN 105294409 A 2/2016
FR 2302991 A1 10/1976

OTHER PUBLICATIONS

Kuntz, Emile et al. "Palladium TPPTS catalyst in water: C-allylation of phenol and guaiacol with allyl alcohol and novel isomerisation of allyl ethers of phenol and guaiacol" Journal of Molecular Catalysis A: Chemical (2006) 244, 124-138 (15 pages).
Sharghi, Hashem et al. "Application of a new phosphorus-free palladium heterogeneous nanocatalyst supported on modified MWCNT the highly selective and efficient cleavage of propargyl, allyl, and benzyl phenol ethers under mild conditions" Molecular Diversity volume (2015) 19, pp. 481-500 (20 pages).
Sanz, Roberto et al. "Selective O-Deallylation of o-Allyloxyanisoles" Synlett 2008 (13): 1957-1960 (4 pages).
Gärtner, Dominik et al. "Highly practical iron-catalyzed C—O cleavage reactions" Catal. Sci. Technol. (2013) 3, 2541-2545 (5 pages).
International Search Report issued in International Application No. PCT/EP2021/057198 dated May 18, 2021 (3 pages).
Written Opinion issued in International Application No. PCT/EP2021/057198 dated May 18, 2021 (6 pages).

*Primary Examiner* — Ana Z Muresan
(74) *Attorney, Agent, or Firm* — Osha Bergman Watanabe & Burton LLP

(57) ABSTRACT

The present invention relates to a process for manufacturing para-eugenol and/or ortho-eugenol, comprising a step (i) of deallylation of at least one compound of formula (I):

Formula (I)

in which $R_1$ and $R_2$ are different, and are chosen from the group consisting of hydrogen and an allyl group ($—CH_2—CH{=}CH_2$).

11 Claims, No Drawings

PROCESS FOR PRODUCING PARA-EUGENOL AND/OR ORTHO-EUGENOL

FIELD OF THE INVENTION

The present invention relates to a process for manufacturing para-eugenol and/or ortho-eugenol, comprising a step (i) of deallylation of at least one compound of formula (I):

Formula (I)

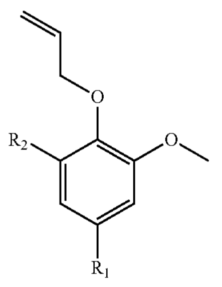

in which $R_1$ and $R_2$ are different, and are chosen from the group consisting of hydrogen and an allyl group ($-CH_2-CH=CH_2$), characterized in that step (i) is performed in the presence of a solvent or a solvent/water mixture.

PRIOR ART

Eugenol is a major aromatic compound of many essential oils such as essence of clove. Eugenol is frequently used in perfumery, but it also has antiseptic, antibacterial, analgesic and antioxidant properties. Eugenol and ortho-eugenol may also be used as synthetic intermediates: for example, eugenol may be used for the preparation of vanillin.

In view of this broad field of exploitation, it is necessary to produce eugenol on an industrial scale and to have available optimized manufacturing processes.

Eugenol is conventionally of natural origin, extracted from plants. The extraction may notably be performed by hydrodistillation, microwave-assisted extraction or extraction with a supercritical fluid. Eugenol of natural origin is generally in the form of a composition comprising a mixture of para-eugenol and ortho-eugenol in a 99/1 (para/ortho) ratio.

Eugenol may also be obtained via a chemical process as described in FR 2 302 991, in which guaiacol is allylated in the presence of allyl chloride and a catalyst.

CN 105294409 describes an alternative synthetic process which uses a composite catalyst based on copper and cobalt.

When these synthetic processes are used, several side reactions may take place, notably leading to the formation of O-allylation compounds, notably corresponding to formula (I). As a result, the eugenol purification is complex.

The process according to the present invention allows the efficient manufacture of para-eugenol and/or ortho-eugenol from said O-allylation compounds. Thus, the present invention is directed toward an efficient and improved process for manufacturing para-eugenol and/or ortho-eugenol, notably a process for efficiently transforming O-allylation compounds into para-eugenol and/or ortho-eugenol, on an industrial scale, notably with improved yields.

BRIEF DESCRIPTION

A first subject of the present invention is a novel process for manufacturing para-eugenol and/or ortho-eugenol, comprising a step (i) of deallylation of at least one compound of formula (I):

Formula (I)

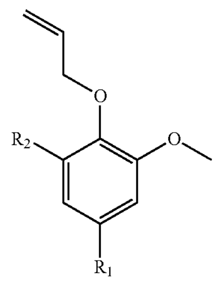

in which $R_1$ and $R_2$ are different, and are chosen from the group consisting of hydrogen and an allyl group ($-CH_2-CH=CH_2$), characterized in that step (i) is performed in the presence of a solvent or a solvent/water mixture.

DETAILED DESCRIPTION

In the context of the present invention, and unless otherwise indicated, the expression "between . . . and . . . " includes the limits. Unless otherwise indicated, the percentages and ppm are percentages and ppm by mass.

In the context of the present invention, and unless otherwise indicated, the term "ppm" means "parts per million". This unit represents a mass fraction: 1 ppm=1 mg/kg.

In the context of the present invention, and unless otherwise indicated, the term "eugenol" refers to para-eugenol, or 4-allyl-2-methoxyphenol according to formula (IIa):

Formula (IIa)

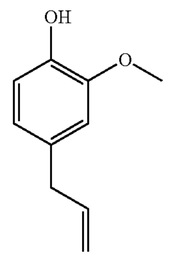

In the context of the present invention, ortho-eugenol refers to 2-allyl-6-methoxyphenol according to formula (IIb):

Formula (IIb)

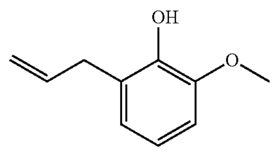

In the context of the present invention, the term "deallylation" refers to a reaction for cleaving a covalent bond between a substrate and an allyl group. Preferably, in the context of the present invention, the deallylation reaction allows the transformation of a compound of formula (I) into a compound of formula (II) according to the following scheme:

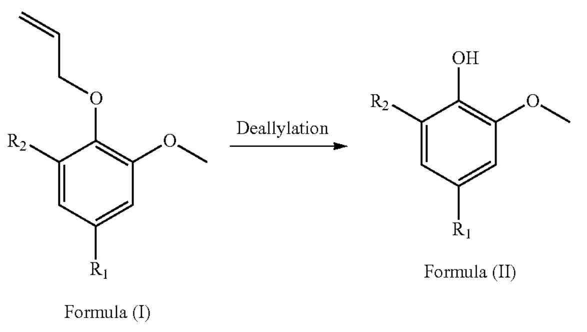

Formula (I)

Formula (II)

in which $R_1$ and $R_2$ have the same meaning as previously. Preferably, in the context of the present invention, the deallylation reaction allows the cleavage of a covalent bond between a carbon atom and an oxygen atom. Advantageously, in the context of the present invention, the deallylation reaction allows the cleavage of an ether bond, in the absence of deallylation of an allyl group attached to a substrate via a covalent bond between two carbon atoms.

By way of example, in the context of the present invention, the deallylation reaction of a compound of formula (Ia) allows the formation of a compound of formula (IIa), preferably in the absence of formation of guaiacol or of guaiacol allyl ether.

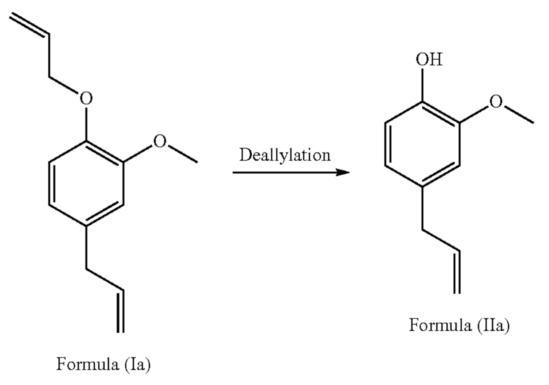

Formula (Ia)

Formula (IIa)

Step (i):

A first subject of the present invention is a process for manufacturing para-eugenol and/or ortho-eugenol, comprising a step (i) of deallylation of at least one compound of formula (I):

Formula (I)

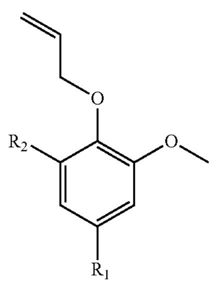

in which $R_1$ and $R_2$ are different, and are chosen from the group consisting of hydrogen and an allyl group ($-CH_2-CH=CH_2$), characterized in that step (i) is performed in the presence of a solvent or a solvent/water mixture.

According to a particular aspect, the process according to the present invention comprises a step of deallylation of a compound of formula (Ia).

Formula (Ia)

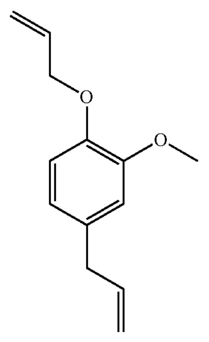

The process according to the present invention allows the formation of a compound of formula (IIa).

Formula (IIa)

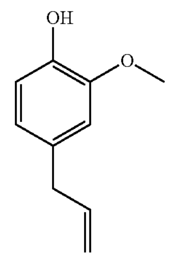

According to another particular aspect, the process according to the present invention comprises a step of deallylation of a compound of formula (Ib).

Formula (Ib)

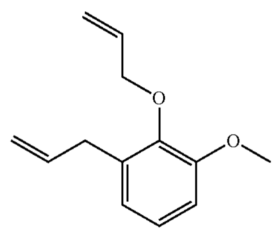

The process according to the present invention allows the formation of a compound of formula (IIb).

Formula (IIb)

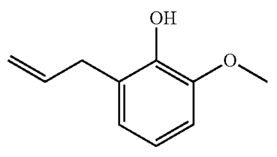

Advantageously, the process according to the present invention comprises a step of deallylation of a mixture comprising at least one compound of formula (Ia) and one compound of formula (Ib).

The process according to the present invention allows the formation of a mixture comprising at least one compound of formula (IIa) and one compound of formula (IIb).

Typically, the process according to the present invention is performed on a composition comprising at least 0.1% by weight of compound of formula (I), preferably at least 0.5% by weight, even more preferentially at least 1% by weight, even more preferentially at least 2% by weight. In general, the process according to the present invention is performed on a composition comprising up to 98% by weight of compound of formula (I), preferably up to 95% by weight, even more preferentially up to 90% by weight. The composition used in the deallylation reaction may comprise 10%, 20%, 30%, 40%, 50%, 60%, 70% or 80% by weight of compound of formula (I).

The process according to the present invention may be performed on a compound of formula (I) alone or as a mixture. Thus, the process according to the present invention may be performed on a composition comprising at least one compound of formula (I). The process according to the present invention may be performed on a composition comprising at least two compounds of formula (I), in particular a compound of formula (Ia) and a compound of formula (Ib).

The composition may also comprise a compound of formula (III).

Formula (III)

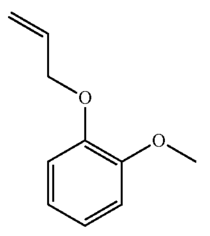

The deallylation process according to the present invention also allows the formation of guaiacol by deallylation of the compound of formula (III).

The process according to the present invention may also be performed on a composition comprising at least two compounds of formula (I), in particular a compound of formula (Ia) and a compound of formula (Ib) and the compound of formula (III). According to the present invention, the process may be performed on a composition also comprising para-eugenol, ortho-eugenol and/or guaiacol.

According to the present invention, step (i) is performed in the presence of a catalyst. Preferably, the catalyst is a catalyst based on platinum, rhodium, iridium, copper, nickel, aluminum, titanium, iron or palladium; preferably, the catalyst is based on platinum or palladium.

Preferentially, step (i) is performed in the presence of Pd/C or Pt/C.

According to the present invention, the amount of catalyst used in step (i) is less than or equal to 30% by weight relative to the total amount of compound of formula (I) and, optionally (III), preferably less than or equal to 25% by weight, very preferentially less than or equal to 20% by weight.

According to the present invention, the amount of catalyst used in step (i) is greater than or equal to 0.1% by weight relative to the total amount of compound of formula (I) and, optionally (III).

Preferably, the amount of catalyst used in step (i) is greater than or equal to 0.5% by weight relative to the total amount of compound of formula (I) and, optionally (III), preferably greater than or equal to 0.5% by weight, very preferentially greater than or equal to 1% by weight and very preferentially greater than or equal to 2% by weight.

According to the present invention, step (i) is performed in the presence of a solvent or a water/solvent mixture. Preferably, the solvent is a polar protic solvent. The solvent may be an alcohol, preferably chosen from MeOH, EtOH, i-PrOH and BuOH.

According to the present invention, step (i) may be performed in the presence of a water/solvent mixture; preferably, the solvent/water weight ratio is between 10/1 and 1/1, preferably between 8/1 and 3/1 and very preferentially between 6/1 and 4/1.

According to the present invention, step (i) is performed in the presence of a base; preferably, the pKa in water is greater than or equal to 8, preferably greater than or equal to 9, very preferentially greater than or equal to 10. The base may be chosen from the group consisting of KOH, NaOH, $K_2CO_3$, $Na_2CO_3$, $Ba(OH)_2$, $Ca(OH)_2$, CsOH and LiOH or a compound of formula $NR_3OH$, in which R is a linear or branched alkyl chain comprising from 1 to 6 carbon atoms. According to a particular aspect, step (i) is performed in the presence of a strong base. In general, step (i) is performed in the presence of KOH, NaOH, $Ba(OH)_2$ or $Ca(OH)_2$.

According to the present invention, the content of base in step (i) is greater than or equal to 5% by weight relative to the amount of solvent used, preferably greater than or equal to 8% by weight. According to the present invention, the amount of base in step (i) is less than or equal to 15% by weight relative to the amount of solvent used, preferably less than or equal to 10% by weight.

According to the present invention, step (i) may be performed at a temperature of greater than or equal to 20° C., preferably greater than or equal to 30° C., preferably greater than or equal to 40° C., very preferentially greater than or equal to 50° C. According to the present invention, step (i) may be performed at a temperature of less than or equal to 100° C., preferably less than or equal to 85° C., very preferentially less than or equal to 70° C. Typically, step (i) may be performed at 65° C. In general, the heating is maintained for a period ranging from 2 hours to 24 hours.

According to the present invention, step (i) is generally performed at atmospheric pressure. Step (i) may also be performed in an autoclave; preferably, the reaction is performed at a pressure greater than or equal to atmospheric pressure, preferably greater than or equal to 2 bar, very preferentially greater than or equal to 5 bar. Preferably, the reaction is performed at a pressure of less than or equal to 50 bar, preferably less than or equal to 20 bar, very preferentially less than or equal to 10 bar.

Typically, the degree of conversion of the compound of formula (I) into compound of formula (II) is greater than or equal to 60%, preferably greater than or equal to 75%, very preferentially greater than or equal to 85% and even more preferentially greater than or equal to 95%.

According to a particular aspect, the process according to the present invention is performed on a composition comprising at least one compound of formula (I) obtained from a process for the allylation of guaiacol in the presence of an allyl halide or an allyl alcohol.

Allylation of Guaiacol

The process for the allylation of guaiacol in the presence of an allyl halide may be performed under the conditions as described in FR 2 302 991 or in CN 105294409. According to another aspect, the process for the allylation of guaiacol in the presence of an allyl alcohol may be performed under the conditions as described in *J. Mol. Cat. A: Chemical,* 2006, 244, 124-138.

In a particular aspect of the present invention, guaiacol is reacted with an allyl halide, preferentially allyl chloride, as described in FR 2 302 991.

This reaction allows the formation of at least one compound of formula (I), notably of formulae (Ia), (Ib) and (III). This reaction also allows the formation of para-eugenol or ortho-eugenol. In particular, the alkylation reaction is performed in the presence of an aqueous solution of an alkali metal, or of an alkaline-earth metal hydroxide, such as NaOH or KOH. In addition, the reaction may be performed in the presence of a catalyst, notably a copper-based catalyst such as CuCl, $CuCl_2 \cdot 2H_2O$, $Cu(NO_3)_2$ or $Cu(OAc)_2 \cdot 2H_2O$. The reaction may also be performed in the presence of a composite catalyst based on copper and cobalt as described in patent application CN 105294409.

Generally, the amount of catalyst is greater than or equal to 0.01% by weight, preferentially greater than or equal to 0.02% by weight, more preferentially greater than or equal to 0.05% by weight and very preferentially greater than or equal to 0.1% by weight relative to the amount of guaiacol. Generally, the amount of catalyst is less than or equal to 10% by weight, preferentially less than or equal to 5% by weight, more preferentially less than or equal to 2% by weight and very preferentially greater than or equal to 1% by weight relative to the amount of guaiacol. Generally, the reaction temperature is greater than or equal to 5° C., preferably greater than or equal to 10° C., more preferentially greater than or equal to 15° C. and very preferentially greater than or equal to 25° C. Generally, the reaction temperature is less than or equal to 95° C., preferably less than or equal to 80° C., more preferentially less than or equal to 65° C. and very preferentially less than or equal to 50° C.

The reaction is generally performed in the presence of an ammonium salt or of ammonia as described in FR 2 302 991. Ammonia may form, with the catalyst, a complex of copper-amine type.

In general, in a first stage, a guaiacol salt is formed in aqueous solution. The catalyst is added to the reaction mixture, followed by the addition of an aqueous ammonia solution, and finally the allyl halide is added to the reaction mixture.

The allylation reaction may be a step prior to step (i) according to the present invention. Advantageously, when the process for manufacturing para-eugenol and/or ortho-eugenol according to the present invention, and comprising a step (i) as described previously, is performed on a composition obtained from a guaiacol allylation reaction, only the compounds of formula (I) and/or (III) are converted into compounds of formula (II) and/or guaiacol, respectively. Thus, on conclusion of the process according to the present invention, the composition of the mixture comprises para-eugenol and/or ortho-eugenol and/or guaiacol. Thus, purification is facilitated. The guaiacol may also be recycled.

In general, on conclusion of the allylation reaction, a two-phase mixture is obtained: an aqueous phase and an organic phase. Advantageously, the pH of the composition obtained from a guaiacol allylation reaction may be adjusted; preferably, the pH is less than or equal to 8.5, preferably less than or equal to 8.

According to a particular aspect, the composition obtained from a guaiacol allylation reaction may be the organic phase obtained on conclusion of the allylation reaction, with optional adjustment of the pH. Typically, the composition comprises at least one compound chosen from the compound of formula (Ia), the compound of formula (Ib), the compound of formula (III), guaiacol, para-eugenol and ortho-eugenol. Said composition is subjected to a step (i) as described previously.

On conclusion of step (i), the composition obtained comprises at least one compound chosen from para-eugenol, ortho-eugenol and guaiacol.

According to one embodiment, the guaiacol is distilled off. The guaiacol may be recycled into the guaiacol allylation reaction. The ortho-eugenol and para-eugenol compounds can then be separated by distillation. Optionally, the distillation may be performed in the presence of at least one antioxidant, such as vitamin E, BHA, BHT, TBHQ or TBC.

According to a particular aspect, the composition obtained from a guaiacol allylation reaction may be the organic phase obtained on conclusion of the allylation reaction, with optional adjustment of the pH. Typically, the composition comprises at least one compound chosen from the compound of formula (Ia), the compound of formula (Ib), the compound of formula (III), guaiacol, para-eugenol and ortho-eugenol. Said composition is subjected to a step (i) as described previously.

On conclusion of step (i), the composition obtained comprises at least one compound chosen from para-eugenol, ortho-eugenol and guaiacol.

According to another embodiment, the guaiacol is distilled off. The guaiacol may be recycled into the guaiacol allylation reaction. The ortho-eugenol and para-eugenol compounds can then be separated by selective salification. The ortho-eugenol and para-eugenol compounds are diluted in a solvent having no acidic nature which is capable of reacting with $K_2CO_3$; preferably, the solvent has a pKa in water of less than or equal to 8.5, preferably less than or equal to 8. Preferably, the solvent is a hydrocarbon solvent of the cyclic or acyclic alkane family.

Preferably, the hydrocarbon solvent of the alkane family is an alkane comprising from 5 to 15 carbon atoms; preferably, the hydrocarbon solvent of the alkane family is chosen from the group consisting of pentane, hexane, heptane, octane, nonane and cyclohexane. $K_2CO_3$ is added to this solution. The mixture is then filtered. The ortho-eugenol is recovered from the filtrate, preferably by evaporating off the solvent. The para-eugenol is obtained in the cake in salified form and may be recovered by acidification.

According to a particular aspect, the composition obtained from a guaiacol allylation reaction may be the organic phase obtained on conclusion of the allylation reaction, with optional adjustment of the pH. Typically, the composition comprises at least one compound chosen from the compound of formula (Ia), the compound of formula (Ib), the compound of formula (III), guaiacol, para-eugenol and ortho-eugenol. Said composition is subjected to a step (i) as described previously.

On conclusion of step (i), the composition obtained comprises at least one compound chosen from para-eugenol, ortho-eugenol and guaiacol.

The ortho-eugenol and para-eugenol compounds can then be separated by selective salification. Optionally, the deallylation solvent may be evaporated off beforehand. The ortho-eugenol and para-eugenol compounds are diluted in a solvent having no acidic nature which is capable of reacting with $K_2CO_3$; preferably, the solvent has a pKa in water of less than or equal to 8.5, preferably less than or equal to 8. Preferably, the solvent is a hydrocarbon solvent of the cyclic or acyclic alkane family. Preferably, the hydrocarbon solvent of the alkane family is an alkane comprising from 5 to 15 carbon atoms; preferably, the hydrocarbon solvent of the alkane family is chosen from the group consisting of pentane, hexane, heptane, octane, nonane and cyclohexane. $K_2CO_3$ is added to this solution. The mixture is then filtered. The ortho-eugenol is recovered from the filtrate, preferably by evaporating off the solvent. The cake comprises at least one compound from among para-eugenol and guaiacol in salified form, and may be recovered by acidification. After acidification, the guaiacol and the para-eugenol may be separated by distillation.

According to another particular aspect, the organic phase obtained on conclusion of the allylation reaction may undergo a selective salification pretreatment. In particular, the organic phase is diluted in a solvent having no acidic nature which is capable of reacting with $K_2CO_3$; preferably, the solvent has a pKa in water of less than or equal to 8.5, preferably less than or equal to 8. Preferably, the solvent is a hydrocarbon solvent of the cyclic or acyclic alkane family.

Preferably, the hydrocarbon solvent of the alkane family is an alkane comprising from 5 to 15 carbon atoms; preferably, the hydrocarbon solvent of the alkane family is chosen from the group consisting of pentane, hexane, heptane, octane, nonane and cyclohexane. $K_2CO_3$ is added to this solution. The mixture is then filtered, and step (i) may be performed on the filtrate. The solvent is generally distilled off beforehand. The filtrate comprises at least one compound chosen from the compound of formula (Ia), the compound of formula (Ib), the compound of formula (III) and ortho-eugenol. In general, the content of para-eugenol and guaiacol in the filtrate, after distilling off the solvent, is less than or equal to 1% by weight relative to the total weight of the filtrate. On conclusion of step (i), the composition comprises at least one compound chosen from para-eugenol, ortho-eugenol and guaiacol. The guaiacol may be distilled off and may be recycled into the guaiacol allylation reaction. The ortho-eugenol and para-eugenol compounds can then be separated by distillation. Optionally, the distillation may be performed in the presence of at least one antioxidant, such as vitamin E, BHA, BHT, TBHQ or TBC.

Thus, according to the present invention, the overall yield for the synthesis of para-eugenol and/or ortho-eugenol comprising:

a step of allylation of guaiacol, a step (i) of deallylation according to the present invention, may be improved by recycling the guaiacol.

EXAMPLES

Example 1: The compound of formula (Ia) (250 mg, 1.22 mmol) is dissolved in KOH (10% by weight in methanol, 25 mL). Pd/C (10% by weight, 50 mg) is added. The mixture is heated at 65° C. for 3 hours.

The degree of conversion of the compound of formula (Ia) into para-eugenol is 95%.

No formation of guaiacol was observed.

Example 2: A reaction mixture obtained from an allylation reaction as described according to patent application FR 2 302 991 comprising a compound of formula (Ia), a compound of formula (Ib), a compound of formula (III), para-eugenol, ortho-eugenol and guaiacol (253 mg) is dissolved in KOH (10% by weight in methanol, 25 mL). Pd/C (10% by weight, 13 mg) is added. After 3 hours of reaction at 65° C., the reaction mixture is analyzed and comprises para-eugenol, ortho-eugenol and guaiacol.

The invention claimed is:

1. A process for manufacturing para-eugenol and/or ortho-eugenol, comprising:

deallylating at least one compound of formula (I) in the presence of a catalyst, a base, and a solvent or a solvent/water mixture to form a deallylated product, wherein the solvent comprises a polar solvent, a protic solvent or a solvent/water mixture, and wherein the deallylating is performed in the presence of a Pd/C or Pt/C catalyst:

Formula (I)

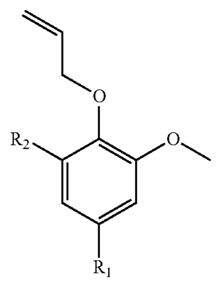

wherein $R_1$ and $R_2$ are different, and are selected from the group consisting of hydrogen and an allyl group $—CH_2—CH═CH_2$, and obtaining the para-eugenol and/or ortho-eugenol from the deallylated product.

2. The process for manufacturing para-eugenol and/or ortho-eugenol as claimed in claim 1, wherein the deallylating comprises deallylating a mixture comprising at least one compound of formula (Ia) and one compound of formula (Ib)

Formula (Ia)

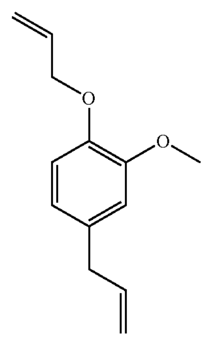

Formula (Ib)

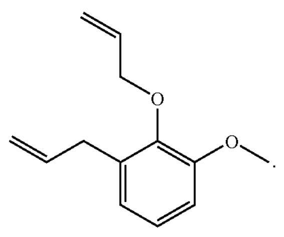.

3. The process for manufacturing para-eugenol and/or ortho-eugenol of claim 1, wherein the deallylating comprises forming guaiacol by deallylating a compound of formula (III):

Formula (III)

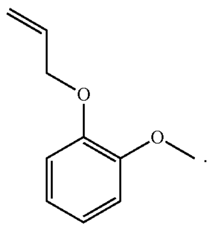

4. The process for manufacturing para-eugenol and/or ortho-eugenol of claim 1, wherein the content of catalyst during the deallylation is between 0.1% and 30% by weight relative to the total amount of compound of formula (I) and optionally of compound of formula (II).

5. The process for manufacturing para-eugenol and/or ortho-eugenol of claim 1, wherein the deallylating is performed in the presence of a water/solvent mixture.

6. The process for manufacturing para-eugenol and/or ortho-eugenol of claim 1, wherein the base has a pKa in water of greater than or equal to 8.

7. The process for manufacturing para-eugenol and/or ortho-eugenol of claim 1, wherein the base is selected from the group consisting of KOH, NaOH, $K_2CO_3$, $Na_2CO_3$, $Ba(OH)_2$, $Ca(OH)_2$, CsOH, LiOH, a compound of formula $NR_3OH$ in which R is a linear or branched alkyl chain comprising from 1 to 6 carbon atoms, and combinations thereof.

8. The process for manufacturing para-eugenol and/or ortho-eugenol of claim 1, wherein the deallylating is performed at a temperature of greater than or equal to 20° C.

9. The process for manufacturing para-eugenol and/or ortho-eugenol of claim 1, wherein the compound of formula (I) is derived from a process for the allylation of guaiacol in the presence of an allyl halide or an allyl alcohol.

10. The process for manufacturing para-eugenol and/or ortho-eugenol of claim 1, comprising at least one step, after the deallylating, of separating the guaiacol, para-eugenol and/or ortho-eugenol.

11. The process for manufacturing para-eugenol and/or ortho-eugenol, comprising:

allylating guaiacol in the presence of an allyl halide, deallylating at least one compound of formula (I) as defined in claim 1, wherein the deallylating is performed in the presence of a Pd/C or Pt/C catalyst, a base, and a solvent or a solvent/water mixture to form a deallylated product, wherein the solvent comprises a polar solvent, a protic solvent or a solvent/water mixture, and separating the guaiacol, para-eugenol and/or ortho-eugenol from the deallylated product.

* * * * *